United States Patent [19]

Aemmer et al.

[11] Patent Number: 4,643,230
[45] Date of Patent: Feb. 17, 1987

[54] METHOD AND APPARATUS FOR THE AUTOMATIC MONITORING OF TEXTILE FABRICS, ESPECIALLY WOVEN FABRICS

[75] Inventors: Peter F. Aemmer, Wettswil; Kurt Aeppli, Uster, both of Switzerland

[73] Assignee: Zellweger Uster, Ltd., Uster, Switzerland

[21] Appl. No.: 724,770

[22] Filed: Apr. 18, 1985

[30] Foreign Application Priority Data

Apr. 24, 1984 [CH] Switzerland ............ 2003/84

[51] Int. Cl.⁴ .................. D03J 1/00; G01N 21/89
[52] U.S. Cl. ...................................... 139/1 B; 250/563
[58] Field of Search ............... 139/1 B, 1 R, 348; 250/562, 563; 364/470; 66/166; 73/159; 26/70

[56] References Cited

U.S. PATENT DOCUMENTS

| | | | |
|---|---|---|---|
| 2,279,759 | 4/1942 | Moore | 139/1 B |
| 3,046,767 | 7/1962 | Nickell | 66/166 |
| 3,417,252 | 12/1968 | Nickell | 250/562 |
| 3,570,550 | 3/1971 | Budzyna | 139/336 |
| 3,613,743 | 10/1971 | Sakamoto | 139/348 |
| 3,657,727 | 4/1972 | Blevins | 250/219 WE |
| 4,103,177 | 7/1978 | Sanford | 250/562 |
| 4,274,748 | 6/1981 | Bortin | 356/431 |
| 4,361,171 | 11/1982 | Fukuda | 139/348 |
| 4,389,575 | 6/1983 | Cole | 250/563 |

FOREIGN PATENT DOCUMENTS

115573 2/1983 European Pat. Off. .

Primary Examiner—Werner H. Schroeder
Assistant Examiner—Joseph S. Machuga
Attorney, Agent, or Firm—Antonelli, Terry & Wands

[57] ABSTRACT

The length of fabric is scanned continuously directly at the weaving machine and any defective variations from the texture judged to be normal are determined and displayed. Scanning is performed by an electrical-optical scanning head traversing across the width of the cloth and in the evaluation of the signals of the scanning head those signals are preferentially treated which represent an excessive variation from a specified size or number, or which have a certain periodicity. The variations of the type mentioned are representative of warp stripes and weft bars and consequently are very serious cloth faults. These cloth faults can now by means of scanning be detected directly at the weaving machine sufficiently early for corrective action to be taken in the weaving process before large quantities of fabric are produced with these faults. Thereby the occurrence of fabric of inferior quality is at least considerably reduced.

8 Claims, 5 Drawing Figures

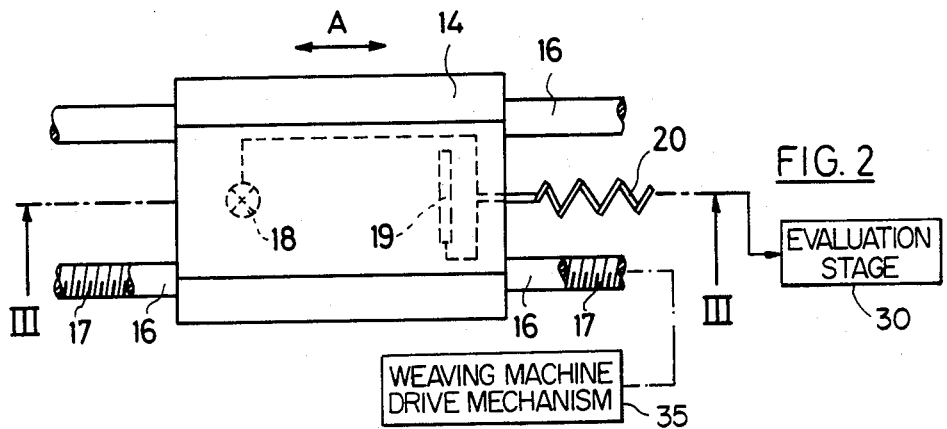
FIG. 2
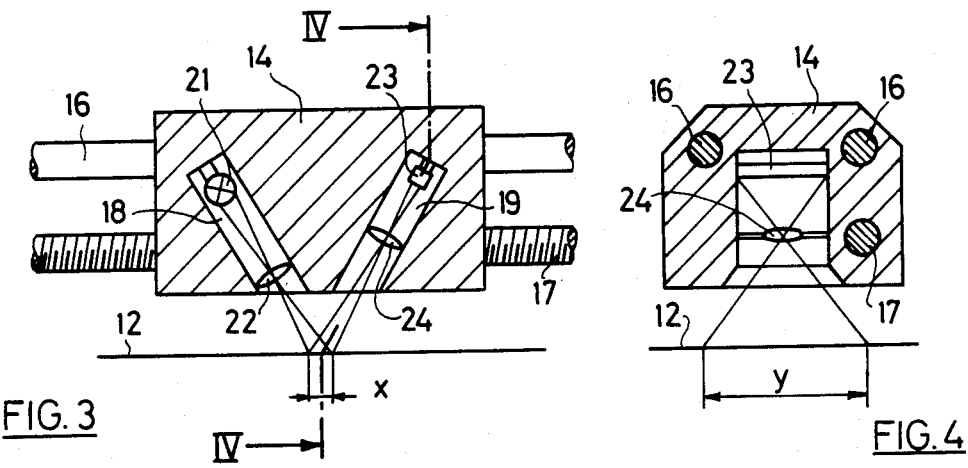
FIG. 3
FIG. 4
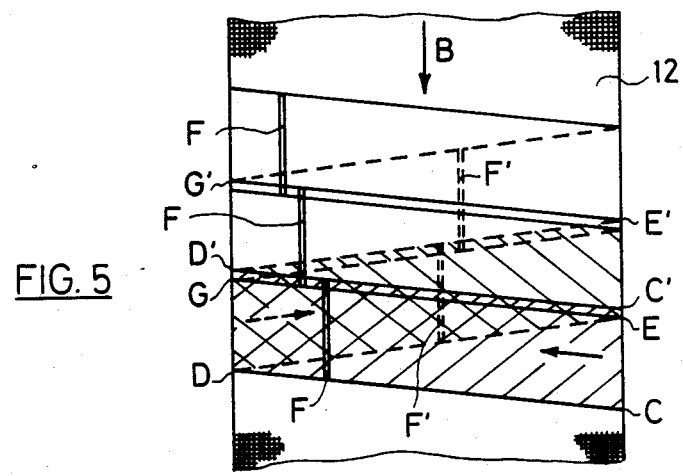
FIG. 5

METHOD AND APPARATUS FOR THE AUTOMATIC MONITORING OF TEXTILE FABRICS, ESPECIALLY WOVEN FABRICS

BACKGROUND OF THE INVENTION

The present invention is directed to a method and apparatus for the automatic monitoring of textile fabrics, especially woven fabrics, in which the woven fabric is continuously scanned by an electrical-optical device immediately at the weaving machine or at a cloth rolling machine located separate from the weaving machine, and defective variations from the texture judged to be normal are detected and displayed.

The present practice in weaving establishments is to examine cloth on cloth inspection tables or cloth inspection machines, in which the cloth is passed over a flat inspection board or over a curved inspection table, and the cloth is visually examined with the aid of illumination from a source built into the inspection board or inspection table. Proposals have already been made for the automation of the arduous inspection duties of the operator by using sensor systems, such as scanning cameras, plane cameras or laser scanners, but because of the costs involved, these sensor systems are typically suited only for one type of cloth inspection table. A common feature of these two types of monitoring systems is that they are used away from the weaving machine and often are employed a relatively long time after the weaving process has veen completed.

When inspecting the fabric, the operator not only has to examine the cloth, but where possible, has to remedy the faults which are detected, which in some cases takes place on special burling and mending tables. When it is not possible to remedy a fault, then the faulty portion must be cut out and at best the cloth can be sold only as second quality.

As it is a constant occurrence for fabrics to contain faults which could have been avoided by action being taken in the weaving process, it has already been often suggested that monitoring of the cloth should take place directly at the weaving machine, as then there would exist the possibility of taking corrective action.

Thus, it is known from U.S. Pat. No. 3,502,115 that an inspection station in the form of a cloth inspection table may be set up directly at the weaving machine, so that faults which could be remedied by modifying the setting of the weaving machine could be detected as early as possible. The required adjustments of the weaving machine could thus be quickly undertaken and the amount of second quality cloth could be reduced. However, when it is considered that the working conditions for operators in the weaving shed are significantly worse than those conditions which prevail in the cloth inspection room in which cloth examination usually takes place, then one would reach the conclusion that this type of cloth inspection will result in an increase rather than a reduction in second quality cloth. Apart from this, the trend in weaving is towards higher productivity. As the production speed of a weaving machine is appreciably lower than the cloth speed during cloth inspection, from this aspect the separation of the weaving process and cloth inspection is economically the more sensible solution. Therefore, this manner of relocation of cloth inspection to the weaving machine would typically be regarded technically as a backward step.

It is known from U.S. Pat. No. 3,613,743 that faults in a fabric may be detected optically by means of a detection apparatus mounted rigidly so as to be stationary on the weaving machine and in which the corresponding fault signals are stored cumulatively together with the length signals representing the length of the cloth. The fault signals are subsequently compared with reference data and a signal is produced when the stored cumulative fault signal exceeds a tolerable limit valve, or when the detected faults are determined to be difficult to remedy. This signal stops the weaving machine and actuates a mechanism for applying a cut mark at the selvedge and for illuminating a warning lamp.

As there is no indication of how the faults may be differentiated by type, i.e., whether they may or may not be repaired, it must be the basis of this known method that the faults per unit length are counted, and when a prescribed value is exceeded, the weaving machine is stopped. However, this results in an increase in the frequency of stoppages of the weaving machine and consequently to a reduction in efficiency without fabric quality being improved or any possibility of making any kind of savings in cloth inspection.

SUMMARY OF THE INVENTION

The purpose of the invention is thus to make significant improvements to the method of cloth inspection and control generally practiced today so that cloth quality is appreciably improved without any resulting loss of efficiency.

The basis of the solution to this problem is the knowledge that cloth inspection at the weaving machine operates most effectively and most efficiently if it responds only to those faults in the fabric which either involve relatively large parts of the fabric or faults which cannot be remedied or prevented by adjustments on the weaving machine.

Characteristic features of the solution to the problem in accordance with the invention are that (a) the electrical-optical device is a scanning head extending over the fabric for scanning the fabric in the weft direction, and (b) in the evaluation of the signals of the scanning head, those signals are preferentially treated which represent an excessive variation from a specified size and/or number and/or have a certain periodicity.

In the evaluation of the signals of the scanning head in accordance with the invention, a classification process is undertaken in which those signals are given preference which represent an excessive variation from a specified size or number, or which have a certain periodicity.

These variations correspond more particularly to the serious fabric faults, such as warp stripes and weft bars, which usually cover a relatively large area of the length or width of the fabric, and in which warp stripes, especially in the case of projectile weaving machines, occur periodically across the weft direction of the fabric. Warp stripes are an especially undesirable fabric fault because firstly they can only be detected visually with extreme difficulty under the conditions prevailing in the weaving shed and secondly they can reduce long lengths of fabric to second quality goods.

In accordance with a first embodiment of the method in accordance with the invention, in the evaluation of the signals of the scanning head, the signals of the various monitoring devices fitted to the weaving machine, such as warp and weft motions, are taken into account.

This action can help to further improve cloth quality by, for example, increasing the sensitivity in the evaluation of the signals of the scanning head after every machine stoppage caused by a signal from a warp or weft stop motion, in such a way that these starting points are positively detected and displayed. This is a significant improvement over the present situation where starting points are frequently not detected in the weaving shed by only a first cloth inspection, which can result in considerable cloth wastage.

According to a second embodiment of the method in accordance with the invention, for the evaluation of the signals of the scanning head, data specific to the manufacturing process of the fabric in question is taken into account. Data of this kind may be for example, the change from an empty weft yarn package to the next full one, where it may be monitored whether the correct weft yarn is used, or also data relating to the selvedges at the edge or within the fabric so that these are not assessed as defective varations because of their different texture.

In the case of structured or multi-colored fabrics, it is possible to consider data relating to the target structure or color, respectively. This means that the evaluation of the signals contains information on intentional variations, and consequently, it is also possible to detect faults in structured or multi-colored fabrics.

The invention also concerns an apparatus for performing the above-mentioned method, having an illumination unit directed towards the fabric to be monitored, a sensor unit and an evaluation stage connected to the sensor unit.

Characteristic features of the apparatus in accordance with the invention are that the sensor unit can be moved transversely to the length of the fabric and thus in the weft direction, that the signal of the sensor unit each time is representative of a scanning zone of elongate form in which the longer dimension of this scanning zone is oriented in the direction of one of the fabric axes, preferably in the warp direction, and that a means is provided for establishing the scanning zone.

BRIEF DESCRIPTION OF THE DRAWINGS

The invention will now be explained in greater detail with reference to the accompanying drawings in which:

FIG. 2 is a plan view of the monitoring apparatus of FIG. 1;

FIG. 3 is a section across the line III—III of FIG. 2;

FIG. 4 is a section across the line IV—IV of FIG. 3; and

FIG. 5 is a plan view of a piece of fabric for explanation of the function of the invention.

DESCRIPTION OF THE PREFERRED EMBODIMENT

Figure 1:
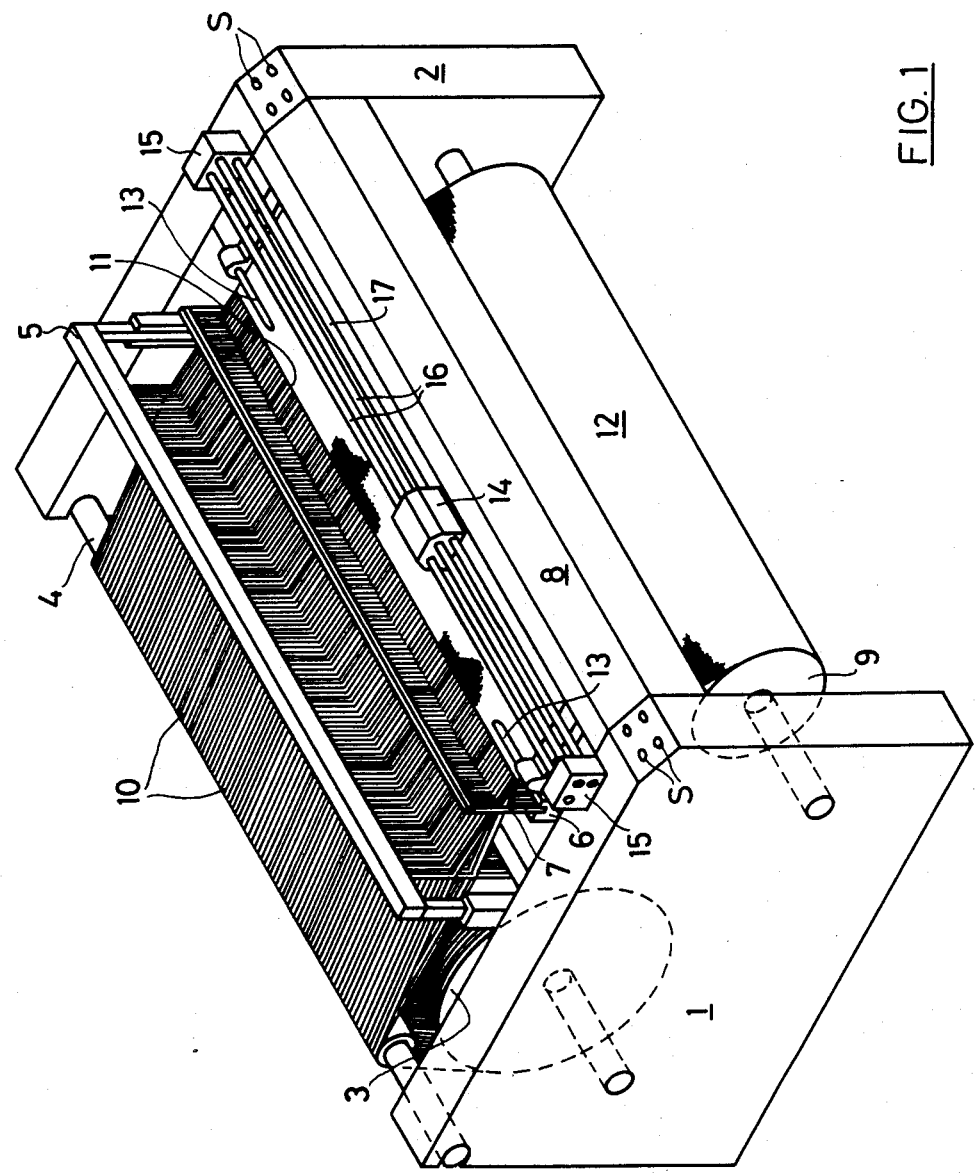
FIG. 1 is a perspective view of a weaving machine equipped with a monitoring apparatus in accordance with the present invention.

The weaving machine shown in FIG. 1 consists of lateral machine walls 1 and 2, a warp beam 3, a backrest 4, a shed forming mechanism 5, a weaver's reed 7 attached to an oscillating sley 6, a breast beam 8 and a cloth beam 9. On the two machine walls 1 and 2 there is an operating surface in the form of a console with a number of switches S for various operating modes of the weaving machine.

From the warp beam 3 the warp threads 10 run in known manner to the fell of the cloth 11 at which the inserted weft threads are each time beaten up by the reed 7. The fabric formed in this way is indicated by 12. In the direction of travel of the fabric 12 immediately after the fell of the cloth 11, a template 13 is attached at each of the two edges of the fabric to a temple holder, which in turn is mounted on a bracket fitted to the machine walls.

As the method of weft insertion is not significant to the invention, this has not been represented in the drawing. The method in accordance with the invention can be used on any type of machine for the manufacture of textile or textile-like fabrics, especially on all single-phase and multi-phase weaving machines with all types of weft insertion systems such as shuttles, projectiles, air, water and the like.

In the zone between the temples 13 and the breast beam 8 in which the fabric 12 is freely accessible from above, there is fitted over the fabric a scanning head 14 which is able to traverse over the fabric width in the direction of the double arrow A (FIG. 2) for monitoring the cloth. In accordance with the drawing, a bearing block 15 is mounted in each of the machine walls 1, 2 and in the two bearing blocks 15 are supported two guide rods 16 and a screw-threaded spindle 17. The purpose of the guide rods 16 is to guide the scanning head 14 and the purpose of the screw-threaded spindle 17 is to drive it in its traversing motion to and fro across the cloth width. The scanning head is thus driven in the manner of the sliding head of a center lathe. The screw-threaded spindle 17 is itself connected to a drive, which preferably is taken from the main driver 35 of the weaving machine, so that the speed of rotation of the screw-threaded spindle 17 and consequently the rate of traverse of the scanning head 14 are in a positive ratio to the speed of running of the weaving machine and thus to the number of picks inserted per minute, and thus to the rate of take-up of the cloth 12.

The construction of the scanning head 14 will now be explained in greater detail with the aid of FIGS. 2 to 4. In accordance with the illustration this consists of a housing through which pass the two guide rods 16 and the screw-threaded spindle 17, the housing being provided with an illumination unit 18 and a sensor unit 19, the two being connected by a coiled cable 20 to a power supply (not shown) or to an evaluation stage 30 supplying the necessary power to the sensor unit. In the latter, the electrical signals which occur are processed in known manner by analog or digital means, for example in the way described in U.S. application Ser. No. 559,802 and in the literature sources quoted in this patent application. As the evaluation of electrical signals obtained by the optical scanning of a laminar surface is within the knowledge of those skilled in this art and is generally known, the evaluation stage is not described in detail.

As may be seen from FIGS. 3 and 4, the light from the illumination unit 18 formed from a light source 21 and a suitable optical system 22 is projected at an oblique angle onto the fabric 12 and the light reflected from the fabric is captured by the sensor unit 19 consisting of a photo-sensitive cell, for example a photodiode 23, and an optical system 24 which limits the light reaching the sensor unit 19 to light from the source 21 that is reflected from the fabric 12. The design of the illumination unit is such that a linear scanning spot of width x and length y is formed on the fabric, the length y of the scanning line being in the direction of the warp threads 19 (FIG. 1) and thus also in the direction of take-up of the cloth 12 (FIG. 5, Arrow B). The sensor unit 19 is of a form suitable for the evaluation of the scanning lines and may for example be a photodiode of appropriate form or also a line of photodiodes. It is also possible to produce the effect electronically by a suitable shadow mask in the evaluation stage in the manner described in the Swiss Patent Application already quoted.

FIG. 5 shows a diagram of the continuous scanning of the fabric 12 manufactured on the weaving machine, the fabric being taken-up in the direction of the arrow B. It is assumed that the scanning head 14 is initially located at the right-hand edge of the cloth with the scanning line between points C and C'. The scanning head 14 is then moved to the left in the direction of the arrow shown. The scanning line F thus extends over the shaded area from C, C' to D, D'. From the line DD' drawn in dotted form the scanning head 14 traverses for the return movement in the direction of the arrow drawn in dotted form towards the right as far as the line EE' and from there again moves towards the left as far as the line GG', and so forth.

As may be gathered from the diagram, the fabric 12 is scanned without any gaps, the scanning zones overlapping both between a consecutive to and fro traverse of the scanning head 14 and also between adjoining movement in the same direction. The latter are shown by the narrow overlapping strips from EC' to GD' and on the other overlap strips of this kind in the drawing.

In a specific practical embodiment, the width x of a scanning line is approximately 1 mm and the length y is dependent firstly on the envisaged number of scanning cycles per minute each consisting of a forward and return traverse of the scanning head 14, and secondly on the weft insertion rate of the weaving machine, thus on the amount of fabric produced per minute, or in other words, the rate of advance of the fabric. Assuming that a modern jet weaving machine of about 2 meters reed width is driven at a machine speed of 500 r.p.m., then the rate of fabric advance when weaving a viscose lining fabric or a cambric shirting fabric is about 20 cm per minute. If the scanning head 14 operates at one scanning cycle per minute, then this corresponds to a fabric advance of 20 cm and the length y of a scanning line would be—without overlap strips—20 cm. In order to attain an overlap strip each time, y is adopted at somewhat greater than 100% of the fabric advance per scanning cycle, for example approximately 110–120% of it.

As already indicated, the application of the monitoring system described is not restricted to weaving machines and of course when used on weaving machines the scanning head 14 does not need to be arranged in the manner shown in FIG. 1. For example, the scanning head 14 could operate also with transmitted light, or it could also be located underneath the fabric 12 in a suitable guide in the machine bed and traversed to and fro. If the cloth beam is not mounted in the weaving machine in the manner shown in FIG. 1 but instead a large roll batching unit is used, then scanning of the fabric could also take place in the zone between the breast beam of the weaving machine and the large roll. Furthermore, in place of a single scanning head it would be possible to use several, for example two, scanning heads.

At the output of the sensor unit 19 (FIGS. 3, 4) characteristic light intensity values occur for the individual scanning lines F, F' (FIG. 5), which following pre-filtering are transferred to a are transferred to the evaluation stage where the values are the compared to preset values, i.e., those values that represent the normal texture or those values specific to the manufacturing process. After the comparison stage, the signals are transferred to a threshold value stage where a classification process is undertaken in which those signals are given preference which represent an excessive variation from a specified size, number or periodicity. Every fabric fault which in visual cloth inspection would be recognized as such causes a corresponding change in the light intensity value in the relevant scanning line, which is detected by the threshold value stage and consequently is able to set off a warning signal and if necessary stop the weaving machine. The weaving machine itself also possesses safety devices which stop the machine when a fault occurs and display to the operator that a weaving fault needs to be repaired. These safety devices are known as warp stop motions, harness monitors and weft stop motions.

As a consequence of the scanning lines F, F' being oriented in the warp direction, the signals obtained in the evaluation unit are especially suitable for detecting fabric faults running in the warp direction. One of these faults which is particularly damaging to cloth quality is warp stripiness, which may be caused for example by faults in the reed or by elements which move in and out of the shed during weaving, such as for instance the guide teeth of a projectile weaving machine. In both cases the warp stripes extend over a long length of the fabric and are thus of a certain size, and in the case of the second phenomenon they additionally occur periodically. As these faults have a very damaging effect on cloth quality and consequently cause a great deal of cloth wastage, it is essential that they should be detected by the monitoring process described. For this purpose, preferential treatment is given to those fault signals which represent a fabric fault of determined size, or number or which occur periodically. The extent is detected by the difference between the measured light intensity value per scanning line and the threshold value and/or by a variation of this kind occurring repeatedly at the same place within several scanning cycles. Numbers and periodicity are detected by the number or periodic occurrence of a fault signal within one scanning cycle.

Although the scanning lines F, F' (FIG. 5) are oriented in the warp direction, weft faults such as starting places or weft bars are also detected. For this purpose, the signals of the sensor unit are each time for at least one of the strip-form scanning zones running transversely across the width of the cloth fed into a buffer store and then sequentially sorted in a suitable manner. As this type of signal processing is known to those skilled in this art, it is not described in greater detail here.

As starting points also represent a very undesirable type of fabric fault but are capable of being fully or partially prevented by adjustment of warp tension, it is essential that these also should be detected. It has been shown that this may be ensured by increasing the sensitivity of the evaluation stage on starting up the weaving machine after a machine stoppage. This is most simply performed by linking the various safety devices of the weaving machine with the scanning head or with the evaluation unit and increasing the sensitivity automatically via the stop signal of the safety device for a certain number of scanning cycles following the starting up of the weaving machine.

Besides the signals of the safety devices, it is also possible to consider other data specific to the manufacturing process of the fabric in question in the evaluation of the signals of the sensor unit 19 (FIG. 3). Such data may for example be signals from a monitor detecting the change from an empty weft package to a full one, by which signals the sensitivity of the evaluation stage would be increased for a few scanning cycles. This method would also monitor whether the full weft package is supplying incorrect yarn. Other such data could involve the selvedges of the cloth, so that for example center selvedges are not assessed as defective variations because of their different texture.

In the case of structured or multi-colored fabrics, data on the target structure or color can be taken into account. This means that the evaluation process of the signals contains information on intentional variations.

What is claimed:

1. Method for the automatic monitoring of textile fabrics, especially woven fabrics, comprising the steps of:
    continuously scanning the woven fabric by means of an electro-optical device including a scanning head traversing across the width of the fabric immediately at the weaving machine on which the fabric is produced by scanning linear scanning zones of the fabric with an elongate detection area, the longitudinal direction of which is oriented in the warp direction so that an output signal is produced from the scanning head indicative of the texture of the surface of the fabric; and
    detecting variations in the normal texture of the fabric by evaluating the signals produced by said scanning head to classify said signals by giving priority to signals which represent variations beyond a predetermined amount greater than zero in size or number, or which have a certain periodicity in said texture.

2. Method in accordance with claim 1, wherein said step of detecting variations includes not only the evaluation of the signals of the scanning head, but also the evaluation of signals of various monitoring devices on the weaving machine, including warp and weft stop motion monitoring devices.

3. Method in accordance with claim 1, wherein the evaluation of the signals of the scanning head to detect defective variations includes evaluation of data specific to the manufacturing process of the woven fabric.

4. Method in accordance with claim 1, wherein for the positive detection of starting places in the fabric, the evaluation sensitivity is increased for a certain number of scanning cycles after the starting-up of the weaving machine.

5. Apparatus for the automatic monitoring of textile fabrics, especially woven fabrics, comprising:
    electro-optical means including a scanning head to be mounted on a weaving machine on which the fabric is produced for continuously scanning the woven fabric, said scanning head including a lighting unit directed towards the fabric to be monitored and a sensor unit for producing a detection signal representative of the texture of the fabric in an elongate area of the fabric in response to receipt of light from said lighting unit reflected by said fabric in said elongate area;
    scanning means coupled to said scanning head for scanning said elongate area over said woven fabric by causing said scanning head to scan said fabric on the weft direction transversely to the length of the cloth; and
    evaluation means connected to receive said detection signal for detecting variations in the normal texture of the fabric by evaluating said detection signal to classify said signal by giving priority to values which represent variations beyond a predetermined amount greater than zero in size or number, or which have a certain periodicity in said texture.

6. Apparatus according to claim 5, wherein said electro-optical means includes an optical device positioned with respect to said sensor unit to limit the light reaching said sensor unit to light reflected from said elongate area.

7. Apparatus according to claim 5, wherein said scanning means is coupled to the main drive of the weaving machine, so that the drive of the scanning head is derived from the weaving machine.

8. Apparatus according to claim 5, wherein the width of said elongate area is approximately 1 mm and its length is greater than the amount of advance of the fabric in the direction of the fabric length during a scanning cycle which corresponds to one forward and backward movement of the scanning head over the width of the fabric.

* * * * *